United States Patent [19]
Chase et al.

[11] Patent Number: 5,928,475
[45] Date of Patent: Jul. 27, 1999

[54] HIGH RESOLUTION SYSTEM AND METHOD FOR MEASUREMENT OF TRAVELING WEB

[75] Inventors: Lee Chase, Los Gatos; John D. Goss, San Jose, both of Calif.; Graham V. Walford, Oakridge, Tenn.; John Preston, Los Altos, Calif.

[73] Assignee: Honeywell-Measurex, Corporation, Cupertino, Calif.

[21] Appl. No.: 08/933,161

[22] Filed: Sep. 18, 1997

Related U.S. Application Data

[63] Continuation-in-part of application No. 08/766,864, Dec. 13, 1996.

[51] Int. Cl.$^6$ .............................. D21F 11/00; G01R 27/02
[52] U.S. Cl. ........................ 162/198; 162/252; 162/258; 162/259; 162/262; 162/263; 162/DIG. 6; 162/DIG. 11; 364/471.02; 364/482; 324/664
[58] Field of Search ...................................... 162/198, 262, 162/263, 252, 258, 259, DIG. 6, DIG. 10, DIG. 11; 324/664, 665; 364/471.02, 482

[56] References Cited

U.S. PATENT DOCUMENTS

| | | |
|---|---|---|
| 3,206,642 | 9/1965 | Canter et al. |
| 3,593,128 | 7/1971 | Perry. |
| 3,630,836 | 12/1971 | Bietry et al. |
| 3,636,327 | 1/1972 | Troutman. |
| 3,646,434 | 2/1972 | Norwich. |
| 3,654,075 | 4/1972 | Keyes et al. |
| 3,713,966 | 1/1973 | Lippke. |
| 3,723,865 | 3/1973 | Batey et al. |

(List continued on next page.)

FOREIGN PATENT DOCUMENTS 0276106  7/1988  European Pat. Off. .

OTHER PUBLICATIONS

Smook, G.A., Handbook for Pulp & Paper Technologist, 2d. ed., (Angus Wilde Publications), pp. 228–9, 1992.
Smook, G.A., Handbook for Pulp & Paper Technologist, 2d. ed., (Angus Wilde Publications), 1992, pp. 228–9.

*Primary Examiner*—Peter Chin
*Assistant Examiner*—Steven B. Leavitt
*Attorney, Agent, or Firm*—Burns, Doane, Swecker & Mathis LLP

[57] ABSTRACT

A system and method that combine an array of fast under wire water weigh sensors with a scanning system provides an accurate measurement of the entire sheet down to 1 in. by 1 in. resolution. Because CD profiles are obtained instantaneously, MD and CD variations are completely decoupled, even if CD profiles are taken at longer intervals apart. The technique allows monitoring the basis weight of a sheet of material that is formed in a process that employs a de-watering machine that includes a water permeable moving fabric supporting wet stock and a dry end which technique includes the steps of: a) positioning an array of water weight sensor elements (array) underneath and adjacent to the fabric wherein the array is positioned in a cross direction to the moving fabric; b) positioning a scanning sensor at the dry end to measure the dry basis weight of the sheet of material; c) operating the machine and measuring the water weights of the sheet of material with the array and measuring the dry basis weight of the sheet of material with the scanning sensor at the dry end; d) developing a functional relationship between water weight of the sheet as measured by the array and the basis weight of the sheet which is formed after being substantially de-watered; end; and e) periodically, adjusting the functional relationship using readings from the scanning sensor to compensate for variations due to process parameters. The technique can further include the step of correlating positional readings of the scanning sensor with measurements from the corresponding element in the array to obtain separate calibration for each individual element of the array and step e comprises adjusting the functional relationship obtained in step d and the calibration obtained in to compensate for variations due to process parameters.

23 Claims, 5 Drawing Sheets

U.S. PATENT DOCUMENTS

| | | |
|---|---|---|
| 3,795,984 | 3/1974 | Meyer . |
| 3,811,087 | 5/1974 | Schmelzer . |
| 3,864,626 | 2/1975 | MacLean et al. . |
| 3,986,110 | 10/1976 | Overall et al. . |
| 4,135,151 | 1/1979 | Rogers et al. . |
| 4,259,632 | 3/1981 | Ahtiainen . |
| 4,314,878 | 2/1982 | Lee . |
| 4,329,201 | 5/1982 | Bolton . |
| 4,369,080 | 1/1983 | Johnson . |
| 4,398,996 | 8/1983 | Bolton et al. . |
| 4,468,611 | 8/1984 | Tward . |
| 4,474,643 | 10/1984 | Lindblad . |
| 4,514,812 | 4/1985 | Miller et al. . |
| 4,580,233 | 4/1986 | Parker et al. . |
| 4,588,943 | 5/1986 | Hirth . |
| 4,613,406 | 9/1986 | Gess . |
| 4,680,089 | 7/1987 | Aral et al. . |
| 4,692,616 | 9/1987 | Hegland et al. . |
| 4,707,779 | 11/1987 | Hu . |
| 4,748,400 | 5/1988 | Typpo . |
| 4,786,529 | 11/1988 | Boissevain . |
| 4,791,353 | 12/1988 | Typpo . |
| 4,817,021 | 3/1989 | Sowerby et al. . |
| 4,827,121 | 5/1989 | Vidrine, Jr. et al. . |
| 4,840,706 | 6/1989 | Campbell . |
| 4,845,421 | 7/1989 | Howarth et al. ......................... 324/688 |
| 4,903,528 | 2/1990 | Balakrishnan et al. . |
| 4,909,070 | 3/1990 | Smith . |
| 4,921,574 | 5/1990 | Hu . |
| 4,924,172 | 5/1990 | Homgren . |
| 4,947,684 | 8/1990 | Balakrishnan . |
| 4,957,770 | 9/1990 | Howarth . |
| 4,980,846 | 12/1990 | Chapman . |
| 4,986,410 | 1/1991 | Shields . |
| 4,990,261 | 2/1991 | Ho . |
| 4,994,145 | 2/1991 | Seymour . |
| 5,013,403 | 5/1991 | Chase . |
| 5,020,469 | 6/1991 | Boissevain et al. . |
| 5,021,740 | 6/1991 | Sarr et al. . |
| 5,022,966 | 6/1991 | Hu . |
| 5,045,798 | 9/1991 | Hendrick . |
| 5,052,223 | 10/1991 | Regnault et al. . |
| 5,067,345 | 11/1991 | Mougne . |
| 5,093,795 | 3/1992 | Lewis . |
| 5,122,754 | 6/1992 | Gotaas . |
| 5,124,552 | 6/1992 | Anderson . |
| 5,132,631 | 7/1992 | Klopfenstein et al. . |
| 5,134,380 | 7/1992 | Jonas . |
| 5,170,128 | 12/1992 | Masurat et al. . |
| 5,170,670 | 12/1992 | Fasching et al. . |
| 5,177,445 | 1/1993 | Cross . |
| 5,198,777 | 3/1993 | Masuda et al. . |
| 5,206,599 | 4/1993 | Mayer . |
| 5,208,544 | 5/1993 | McBrearty et al. . |
| 5,225,785 | 7/1993 | Mayer et al. . |
| 5,241,280 | 8/1993 | Aidun et al. . |
| 5,247,261 | 9/1993 | Gershenfeld . |
| 5,262,955 | 11/1993 | Lewis . |
| 5,270,664 | 12/1993 | McMurtry et al. . |
| 5,340,442 | 8/1994 | Gess et al. . |
| 5,400,247 | 3/1995 | He . |
| 5,450,015 | 9/1995 | Mastico et al. . |
| 5,492,601 | 2/1996 | Ostermayer et al. . |
| 5,493,910 | 2/1996 | Hall et al. . |
| 5,539,634 | 7/1996 | He . |
| 5,561,599 | 10/1996 | Lu . |
| 5,563,809 | 10/1996 | Williams et al. . |
| 5,636,126 | 6/1997 | Heaven et al. . |
| 5,658,432 | 8/1997 | Heaven et al. . |

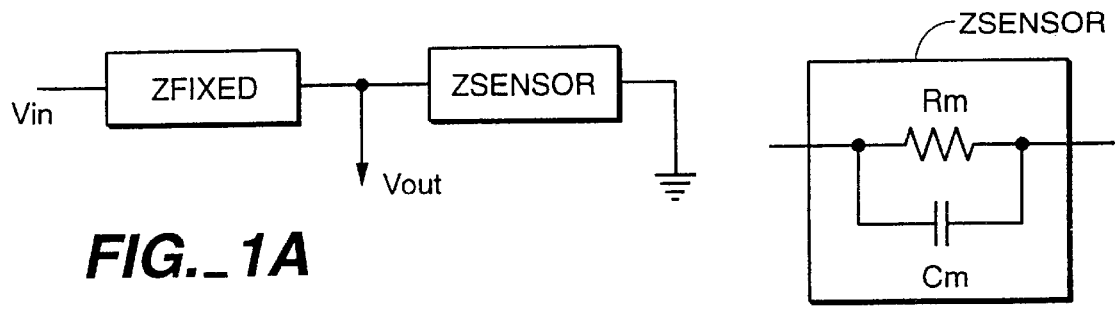
FIG._1A
FIG._1B
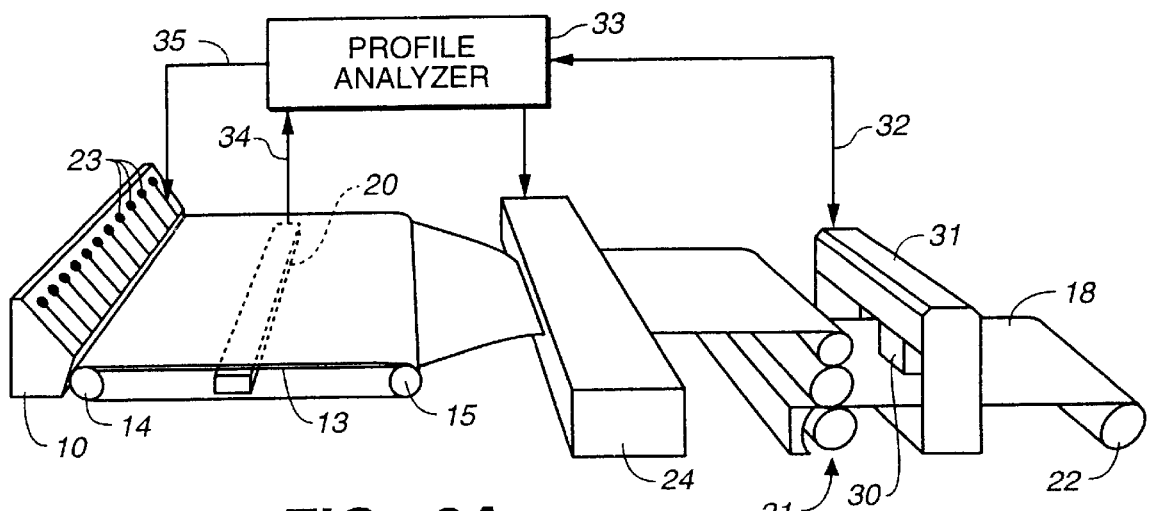
FIG._2A
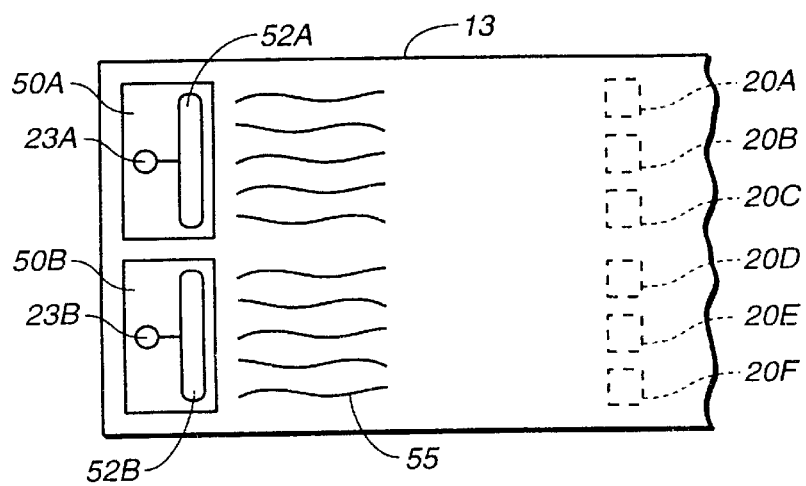
FIG._2B

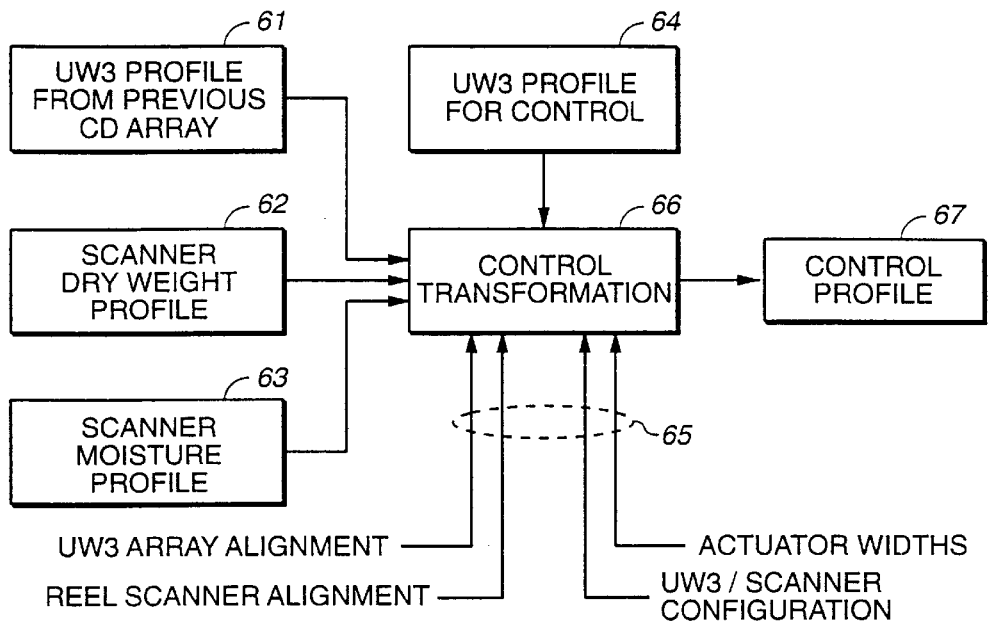
FIG._2C
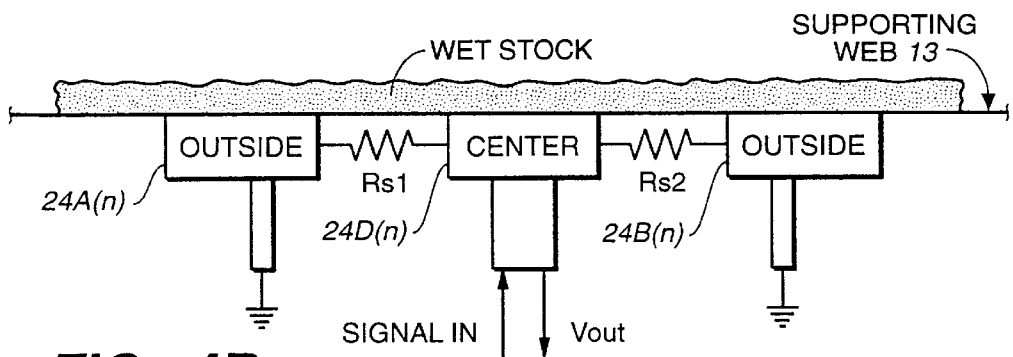
FIG._4B
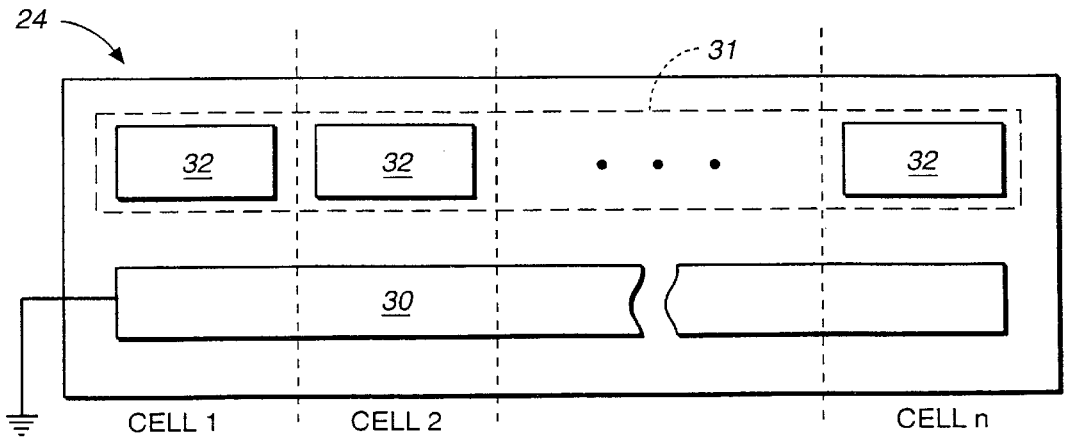
FIG._5A

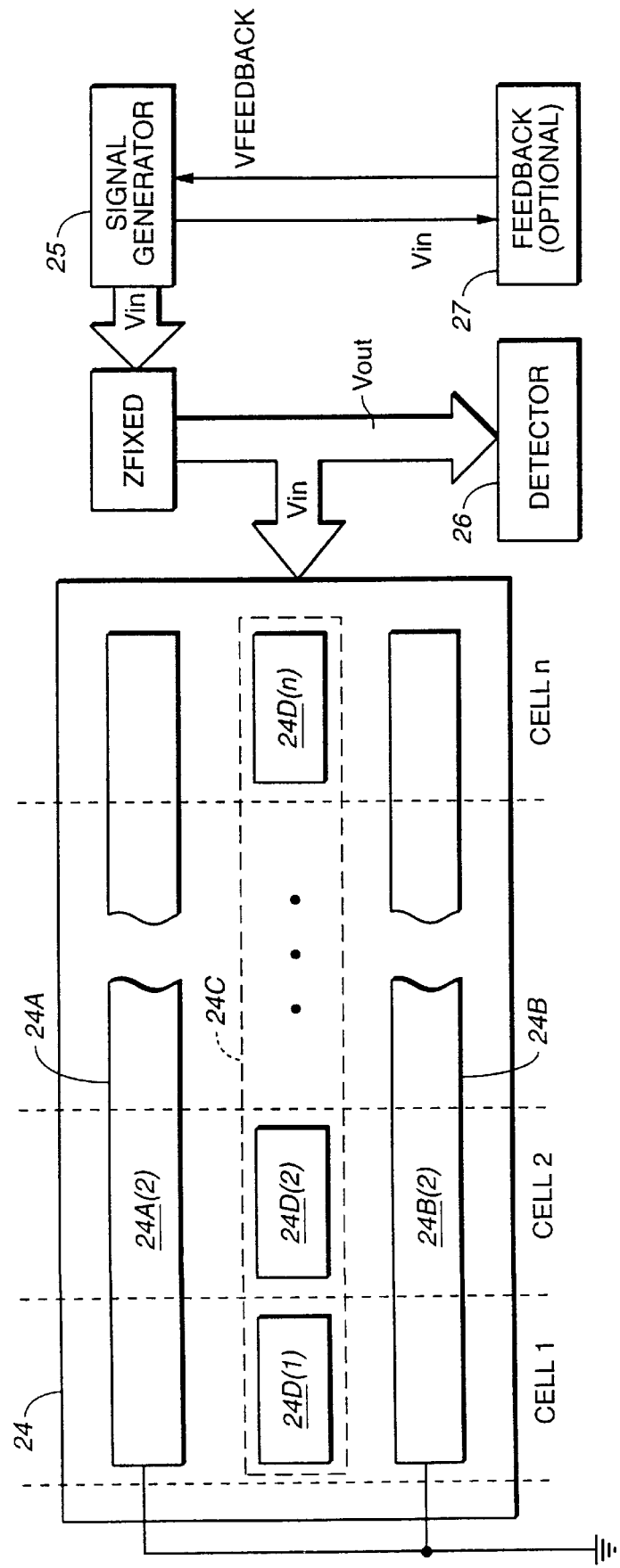
FIG._3

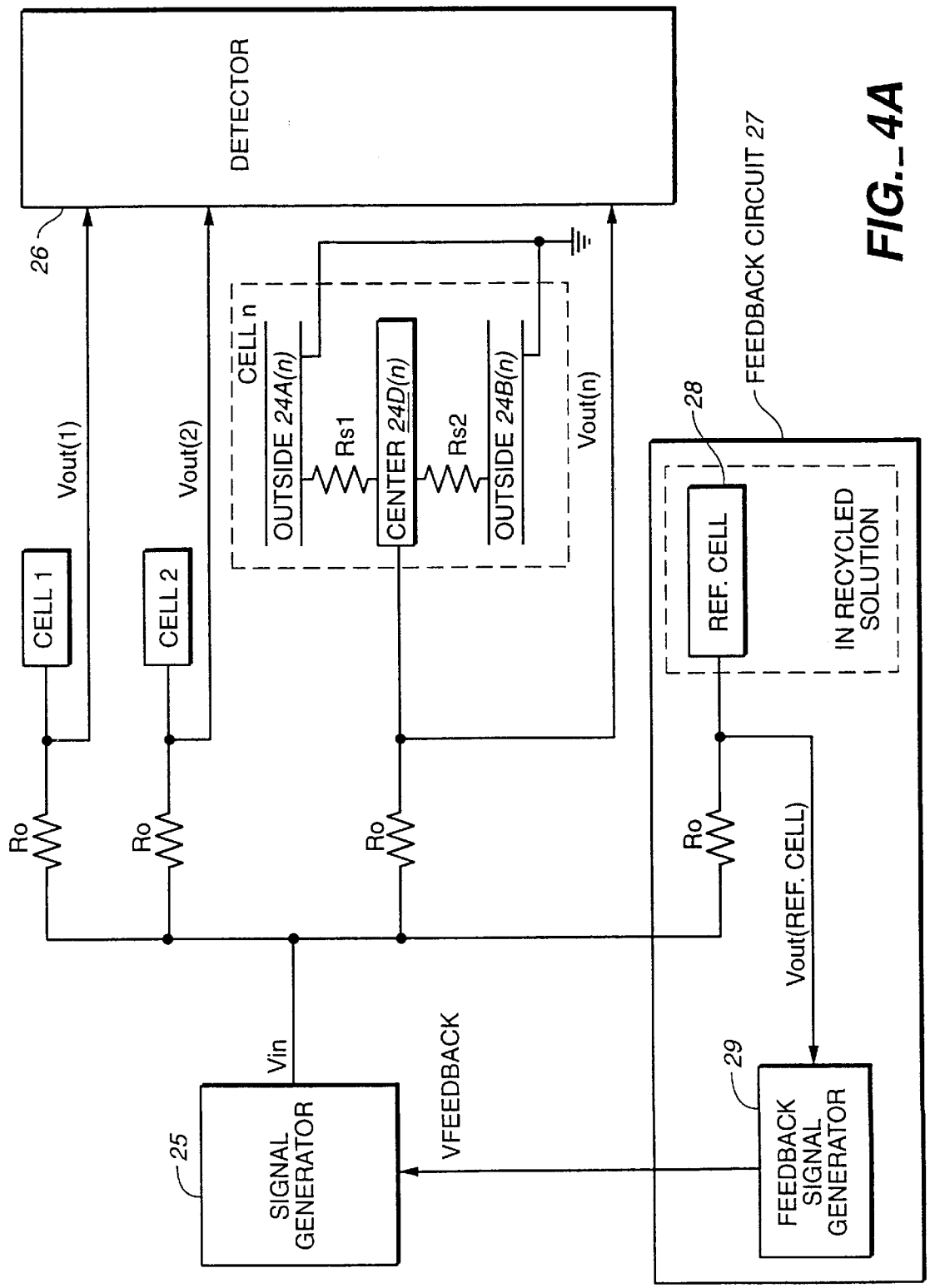

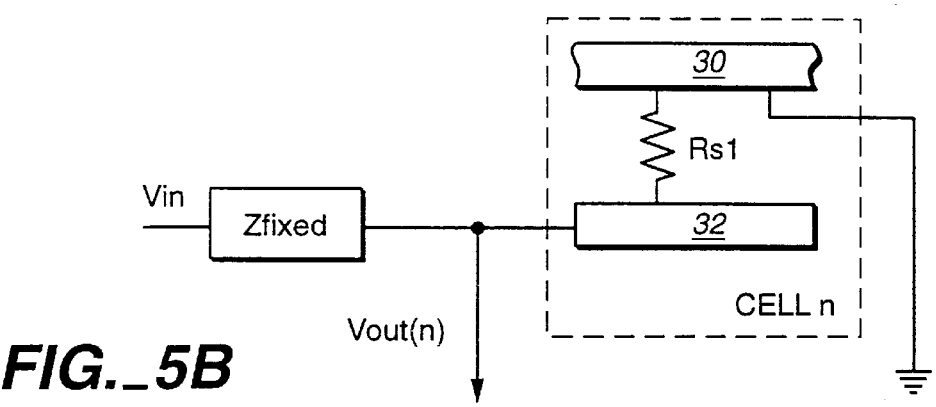
FIG._5B
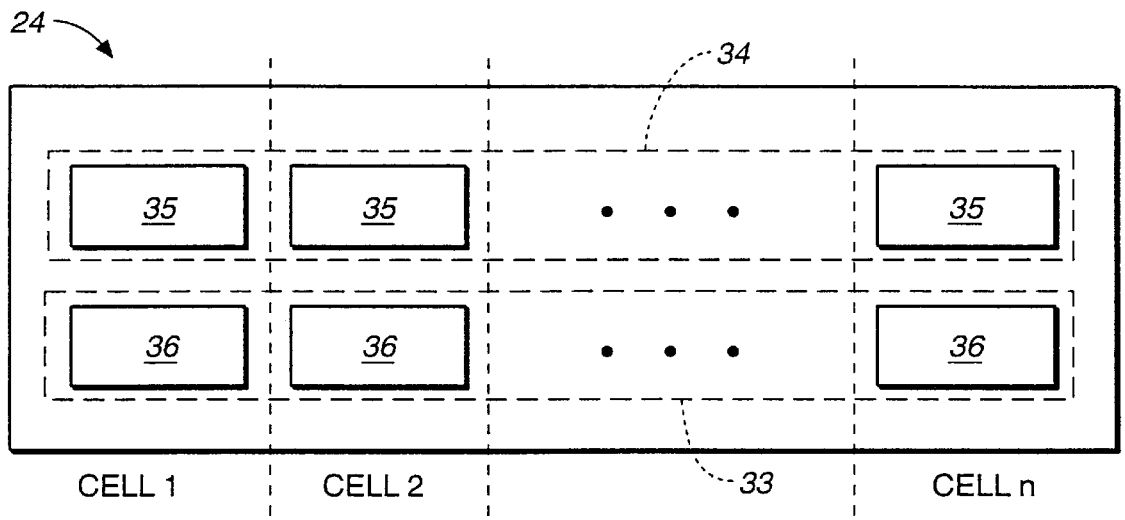
FIG._6A
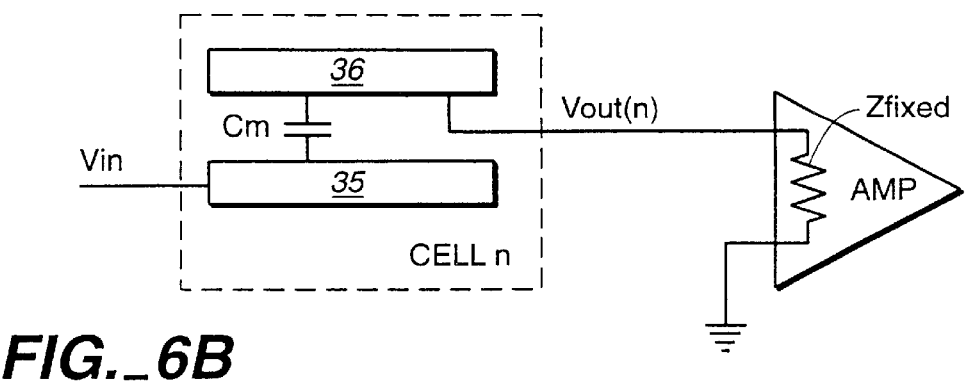
FIG._6B

HIGH RESOLUTION SYSTEM AND METHOD FOR MEASUREMENT OF TRAVELING WEB

REFERENCE TO RELATED APPLICATION

This application is a continuation in part of U.S. application Ser. No. 08/766,864 filed on Dec. 13, 1996.

FIELD OF THE INVENTION

The present invention generally relates to systems for controlling continuous sheetmaking systems and, more specifically, to sensors and methods for measuring and controlling the basis weight of paper in a paper making machine.

BACKGROUND OF THE INVENTION

In the art of making paper with modern high-speed machines, sheet properties must be continually monitored and controlled to assure sheet quality and to minimize the amount of finished product that is rejected when there is an upset in the manufacturing process. The sheet variables that are most often measured include basis weight, moisture content, and caliper (i.e., thickness) of the sheets at various stages in the manufacturing process. These process variables are typically controlled by, for example, adjusting the feedstock supply rate at the beginning of the process, regulating the amount of steam applied to the paper near the middle of the process, or varying the nip pressure between calendaring rollers at the end of the process. Paper making devices well known in the art are described, for example, in "Handbook for Pulp & Paper Technologists" 2nd ed., G. A. Smook, 1992, Angus Wilde Publications, Inc., and "Pulp and Paper Manufacture" Vol III (Paper making and Paperboard Making), R. MacDonald, ed. 1970, McGraw Hill. Sheetmaking systems are further described, for example, in U.S. Pat. Nos. 5,539,634, 5,022,966 4,982,334, 4,786,817, and 4,767,935.

In conventional practice, paper making machines have several control stages with numerous, independently-controllable actuators that extend across the width of the sheet at each control stage. For example, a paper making machine will typically include a head box having a plurality of slices at the front which allow the stock in the head box to flow out on the fabric of the web or wire. The paper making machine might also include a steam box having numerous steam actuators that control the amount of heat applied to several zones across the sheet. Similarly, in a calendaring stage, a segmented calendaring roller can have several actuators for controlling the nip pressure applied between the rollers at various zones across the sheet.

All of the actuators in a stage are operated to maintain a uniform and high quality finished product. Such control might be attempted, for instance, by an operator who periodically monitors sensor readings and then manually adjusts each of the actuators until the desired output readings are produced. Paper making machines include control systems for automatically adjusting cross-directional actuators using signals sent from scanning sensors.

On-line measurements of sheet properties can be made in both the machine direction and in the cross direction. In the sheetmaking art, the term machine direction (MD) refers to the direction that the sheet material travels during the manufacturing process, while the term cross direction (CD) refers to the direction across the width of the sheet which is perpendicular to the machine direction.

Cross-directional measurements are typically made using a scanning sensor that periodically traverses back and forth across the width of the sheet material. Current technology in paper making uses a beta type sensor that scans across the sheet during the manufacturing process, to measure basis weight. The objective of scanning across the sheet is to measure the variability of the sheet in both CD and MD. Based on the measurements, corrections to the process are made to make the sheet more uniform. A difficulty with this measurement technique is that while the sensor scans across 30 to 40 feet of the sheet, CD, 1000 to 2000 feet of paper have passed the sensor in the MD. This means that MD and CD information are mixed together during a scan. Further, the scanning sensor is capable of measuring only a small fraction of the paper produced. Another disadvantage is that the sheet shrinks as it dries, so corrections must be made to determine which actuator at the head box will affect the location being measured.

To separate CD information from the mix, it is typical to filter the data from several scans to average out MD variations. With filtering, it takes several minutes to obtain an accurate CD profile. The MD information is usually extracted by using the average of all readings across the sheet, i.e., "scan average." While these methods have proven reliable and accurate over the years, the main disadvantage is that they are slow and only less than 0.5% of the sheet is actually measured.

As is apparent, there is a need in the art for a system to obtain an accurate, high resolution basis weight measurement for a paper machine, especially one in which the CD profiles are obtained substantially instantaneously, and in which the MD and CD variations are substantially completely decoupled.

SUMMARY OF THE INVENTION

The inventive system and method combine an array of fast under wire water weigh sensors (also referred to as $UW^3$ sensors) with a scanning system to obtain an accurate measurement of the entire sheet typically down to 1 in. by 1 in. resolution. Because CD profiles are obtained instantaneously, whenever profiles are measured, MD and CD variations are completely decoupled. Quality improvements to the sheet fabricated will be achieved by providing fast control of the actuators on the machine and by tuning components on the machine to eliminate the sources of variations. For example, the invention will make it possible to make more uniform paper. Another benefit of the invention is that measurement with the array of $UW^3$ sensors will continue even when there is a sheet break. This allows control to be maintained while the sheet is rethreaded in the machine.

The present invention is based in part on the development of the $UW^3$ sensor which is sensitive to three properties of materials: the conductivity or resistance, the dielectric constant, and the proximity of the material to the $UW^3$ sensor. Depending on the material, one or more of these properties will dominate.

In one aspect, the invention is directed to a system for determining a physical property along the cross direction of a sheet of material that is formed on a de-watering machine that includes a water permeable moving fabric supporting wet stock and a dry end which system includes:

an array of water weight sensor elements (array) that is positioned underneath and adjacent to the fabric wherein the array of water weight sensor elements is positioned to extend transversely of the moving fabric and that generates signals indicative of a profile made up of a multiplicity of water weight measurements at different locations in the cross direction wherein the profile of the water weights is decoupled from machine direction variations.

In another aspect, the invention is directed to a system of controlling the cross directional basis weight uniformity of a sheet of material that is formed on a de-watering machine that includes a water permeable moving fabric supporting wet stock, a dry end, and a headbox having a plurality of slices through which wet stock is introduced onto the fabric, which system includes:

a) an array of water weight sensor elements that is positioned underneath and adjacent to the fabric wherein the array is positioned in a transverse direction to the moving fabric and generates signals indicative of a profile made up of a multiplicity of water weight measurements at different locations in the cross direction;

b) a scanning sensor that is positioned at the dry end to measure the basis weight of the sheet of material as it enters the dry end and that generates signals indicative of a profile of a multiplicity of dry basis weight measurements in the cross direction;

c) means for developing a functional relationship between said water weight measurements and said dry basis weight measurements; and d) means for adjusting the functional relationship in response to subsequent water weight measurements and said dry basis weight measurements.

In a further aspect, the invention is directed to a method of monitoring the basis weight of a sheet of material that is formed in a process that employs a de-watering machine that includes a water permeable moving fabric supporting wet stock and a dry end which includes the steps of:

a) positioning an array of water weight sensor elements (array) underneath and adjacent to the fabric wherein the array is positioned in a cross direction to the moving fabric; and b) operating the machine and measuring the water weights of the sheet of material with the array to generate a cross directional profile of the water weight that is decoupled from machine direction variations.

In the preferred embodiment, the method further comprising the steps of:

c) positioning a scanning sensor at the dry end to measure the dry basis weight of the sheet of material;

d) developing a functional relationship between water weight of the sheet as measured by the array and the dry basis weight of the sheet of material; and e) periodically, adjusting the functional relationship using readings from the scanning sensor to compensate for variations due to changes in operating parameters of the de-watering machine.

The basic embodiment of each $UW^3$ sensor in the array includes a fixed impedance element coupled in series with a variable impedance block between an input signal and ground. The fixed impedance element and the variable impedance block form a voltage divider network such that changes in impedance of the impedance block results in changes in voltage on the output of the sensor. The impedance block represents the impedance of the physical configuration of at least two electrodes within the $UW^3$ sensor and the material residing between and in close proximity to the electrodes. The impedance relates to the property of the material being measured.

In one embodiment, an array which comprises a plurality of the $UW^3$ sensors are positioned across a paper making machine in the CD transverse to MD, and are used to measure the conductivity of an aqueous mixture (referred to as wetstock) in a paper making system. In this case, the conductivity of the wetstock is high and dominates the measurement of the $UW^3$ sensor. The proximity is held constant by contacting the support web in the paper making system under the wet stock. The conductivity of the wetstock is directly proportional to the total water weight within the wetstock, consequently providing information which can be used to monitor and control the quality of the paper sheet produced by the paper making system.

BRIEF DESCRIPTION OF THE DRAWINGS

FIG. 1A shows a basic block diagram of the under wire water weight ($UW^3$) sensor and FIG. 1B shows the equivalent circuit of the sensor block.

FIG. 2A shows a sheetmaking system implementing the technique of the present invention.

FIG. 2B shows the positioning of an array of underwater wire weight sensors in relationship to slices in the head box.

FIG. 2C shows a block diagram of one embodiment of a profile analyzer for generating a control profile.

FIG. 3 shows a block diagram of the $UW^3$ sensor including the basic elements of the sensor.

FIG. 4A shows an electrical representation of an embodiment of the $UW^3$ sensor.

FIG. 4B shows a cross-sectional view of a cell used within the $UW^3$ sensor and its general physical position within a sheetmaking system in accordance with one implementation of the sensor.

FIG. 5A shows a second embodiment of the cell array used in the $UW^3$ sensor.

FIG. 5B shows the configuration of a single cell in the second embodiment of the cell array shown in FIG. 5A.

FIG. 6A shows a third embodiment of the cell array used in the $UW^3$ sensor.

FIG. 6B shows the configuration of a single cell in the third embodiment of the cell array shown in FIG. 6A.

DETAILED DESCRIPTION OF PREFERRED EMBODIMENTS

The present invention employs a system that includes a scanning sensor and an array of sensors that measure water weight across the wire at the wet end of a paper making machine, e.g., fourdrinier. These $UW^3$ sensors have a very fast response time (1 msec) and since there is an array of them, a substantially instantaneous CD profile of water weight can be obtained. The system therefore does not mix MD and CD information and is capable of measuring the entire sheet to 1 in. by 1 in. resolution. Since at the wet end there is practically no sheet (width) shrinkage, measurements at the array elements can be traced directly to control actuators on the head box.

In FIG. 2A, a system for producing continuous sheet material includes processing stages including a headbox 10, a calendaring stack 21 and reel 22. Actuators 23 in headbox 10 discharge raw material through a plurality of slices onto supporting web or wire 13 which rotates between rollers 14 and 15. Foils and vacuum boxes remove water from the material on the wire. Sheet material exiting the wire passes through a dryer 24. A scanning sensor 30, which is supported on supporting frame 31, continuously traverses the sheet and measures properties of the finished sheet in the cross-direction. The finished sheet product is then collected on reel 22. As used herein, the "wet end" portion of the system depicted in FIG. 2A includes the headbox, the web, and those sections just before the dryer, and the "dry end" comprises the sections that are downstream from the dryer.

An array 20 of the $UW^3$ sensors is positioned underneath web 13; by this meant that the sensor is positioned below a portion of the web which supports the wet stock. As further described herein, each of the sensors is configured to measure the water weight of the sheet material as it passes over the array. The array provides a continuous measurement of the entire sheet material along the CD direction at the point where it passes the array. A profile made up of a multiplicity of water weight measurements at different locations in the CD is developed.

In operation of the system, a sheet is traversed from edge to edge by scanning sensor 30 at a generally constant speed during each scan. The time required for a typical scan is generally between twenty and thirty seconds. The rate at which measurement readings are provided by such scanners is usually adjustable; however, a typical rate is about one measurement reading every fifty milliseconds. The scanning sensor is typically controlled to travel at a rate of about 16 inches per second across the sheet. Multiple stationary sensors could also be used. Scanning sensors are known in the art and are described, for example, in U.S. Pat. Nos. 5,094,535, 4,879,471, 5,315,124, and 5,432,353, which are incorporated herein. Such apparatus conventionally uses a gauge mounted on a scanning head which is repetitively scanned transversely across the web. The gauges can use a broad-band infra-red source and one or more detectors with the wavelength of interest being selected by a narrow-band filter, for example, an interference type filter. The gauges used fall into two main types: the transmissive type in which the source and detector are on opposite sides of the web and, in a scanning gauge, are scanned in synchronism across it, and the scatter type (sometimes called "reflective" type) in which the source and detector are in a single head on one side of the web, the detector responding to the amount of source radiation scattered from the web.

Another type of scanning sensor is the nuclear gauge which directs nuclear radiation (beta rays) against a surface of a traveling web while detecting the transmitted radiation. (The quantity of nuclear radiation absorbed over a given area is a measure of the basis weight of the absorbing material.) Nuclear scanning gauges often use radioactive krypton 85 gas or promethium 147 as the beta-ray source. A preferred scanning sensor for the inventive system employs a beta type sensor, and is available from Honeywell-Measurex, Inc., Cupertino, Calif.

As shown FIG. 2A, the system further includes scanning sensor 30 is connected by line 32 to profile analyzer 33. The profile analyzer is a signal processor which includes a control system that operates in response to the cross-directional measurements from array 20 and scanner 30. In operation, scanning sensor 30 provides the analyzer with signals that are indicative of the magnitude of a measured sheet property (e.g., caliper or dry basis weight) at various cross-directional measurement points. Concurrently, the array of $UW^3$ sensors provides the analyzer with the CD water weight profile. The analyzer may also include means for controlling the operation of various components of the sheetmaking system, including, for example, actuators 23.

FIG. 2B illustrates headbox 10 having two slices 50A and 50B which discharge wet stock 55 onto wire 13. The array includes six sensors (20A through 20F). In actual paper making systems, the number of slices in the head box and sensors are much higher. For a head box that is 300 inches in length, there can be 100 or more slices. The rate at which wet stock is discharged through the nozzles 52A and 52B can be controlled by corresponding actuators 23A and 23B, respectively. As the web moves from the head box to the array, wet stock discharged from slice 50A will be measured by sensors 20A, 20B, and 20C, and similarly, wet stock discharged from slice 50B will be measured by sensors 20D, 20E, and 20F.

In one aspect of the present invention, the profile analyzer 33 is implemented as shown in FIG. 2C wherein characteristic profiles such as previous $UW^3$ profile information 61, a scanner dry weight profile 62, a scanner moisture profile 63, and a current $UW^3$ sensor water weight profile 64, along with physical configuration information 65 of the system such as $UW^3$ array alignment, reel scanner alignment, actuator widths, and $UW^3$ and scanner configuration are analyzed and transformed into control information for use by the sheetmaking system. Specifically, control transformation block 66 generates a control profile 67 which can be used to control the operation of the sheetmaking system to compensate for processing variations in the CD direction which is dependent on the obtained $UW^3$ sensor and scanner readings. For instance, the control profile can be used to control the amount of feedstock discharged by each of actuators 23A and 23B. In one embodiment, the control transformation block 66 develops a functional relationship between water weight of the sheet as measured by the $UW^3$ sensor and the dry weight of the sheet as measured by the scanner and correlates positional reading of the dry end scanner with measurements from the corresponding element in the array of water weight sensor elements to obtain separate calibration and hence control for each individual element of the array.

It has been demonstrated that fast variations of water weight on the wire correlate well to fast variations in dry basis weight of the sheet material produced when the water weight is measured upstream from dry line on he wire. The reason is that essentially all of the water on the wire is being held by the paper fibers. Since more fibers hold more water, the measured water weight correlates well to the fiber weight. To use water weight on the wire as an accurate indicator of fiber weight, the calibration is periodically adjusted. The reason for the adjustments is that the relationship between the fiber weight and the water weight will vary as process parameters fluctuate. These parameters include, for example: 1) wire speed, 2) refining, 3) retention aids, 4) wire wear, and 5) fiber type. Since these factors vary relatively slowly, calibration will hold for several minutes. The scanning sensor provides an accurate measurement of fiber weight on a slow time scale, so the water weight to fiber weight calibration can by periodically adjusted. The adjusted water weight measurement then provides a fast, accurate, and high resolution fiber weight measurement of the entire sheet.

Because of the high volume of data produced at the higher resolution (e.g. 1 in. by 1 in.) of the system, it is expected that under normal circumstances, lower MD resolution could be used. That is, CD profiled would be taken at MD intervals greater than 1 inch. However, there are still advantages to the system used with lower MD resolution. Since the CD profile is measured substantially instantaneously, MD variations are not mixed in with the CD measurement. The instantaneous CD profiles are substantially completely decoupled from MD variations.

The calibration is achieved, for example, by correlating approximately 3 minute averages of dry basis weight as measured by the scanning sensor 30 near reel 22 to averages over the same time period of water weight on the wire as measured by the array. Regression analysis of the last 10 averages then would use 30 minutes of data to maintain the correct slope and intercept for the calibration. The sensor array can then provide accurate dry basis weight at up to 600 readings per second.

Another method is to average the dry weight from the scanning sensor on a slice by slice basis and the water weight data for each element of the array. Regression is done between data from each slice (e.g., 50A) and the data from the corresponding array sensors (e.g., 20A, 20B, and 20C). A separate slope and intercept is applied to each set of sensors. One advantage of this method is that factors such as uneven wire wear across the machine can be calibrated out of the final reading. Moreover, by monitoring the differences in calibration, the operators will be alerted when wire wear is excessive.

Under Wire Water Weight ($UW^3$) Sensor

In its broadest sense, the sensor can be represented as a block diagram as shown in FIG. 1A, which includes a fixed impedance element (Zfixed) coupled in series with a variable impedance block (Zsensor) between an input signal (Vin) and ground. The fixed impedance element may be embodied as a resistor, an inductor, a capacitor, or a combination of these elements. The fixed impedance element and the impedance, Zsensor, form a voltage divider network such that changes in impedance, Zsensor, results in changes in voltage on Vout. The impedance block, Zsensor, shown in FIG. 1A is representative of two electrodes and the material residing between the electrodes. The impedance block, Zsensor, can also be represented by the equivalent circuit shown in FIG. 1B, where Rm is the resistance of the material between the electrodes and Cm is the capacitance of the material between the electrodes. The sensor is further described in U.S. patent application Ser. No. 08/766,864 filed on Dec. 13, 1996, which is incorporated herein.

The sensor is sensitive to three physical properties of the material being detected: the conductivity or resistance, the dielectric constant, and the proximity of the material to the sensor. Depending on the material, one or more of these properties will dominate. The material capacitance depends on the geometry of the electrodes, the dielectric constant of the material, and its proximity to the sensor. For a pure dielectric material, the resistance of the material is infinite (i.e. Rm=∞) between the electrodes and the sensor measures the dielectric constant of the material. In the case of highly conductive material, the resistance of the material is much less than the capacitive impedance (i.e. $Rm<<Z_{cm}$), and the sensor measures the conductivity of the material.

To implement the sensor, a signal Vin is coupled to the voltage divider network shown in FIG. 1A and changes in the variable impedance block (Zsensor) is measured on Vout. In this configuration the sensor impedance, Zsensor, is: Zsensor=Zfixed*Vout/(Vin−Vout) (Eq.1). The changes in impedance of Zsensor relates physical characteristics of the material such as material weight, temperature, and chemical composition. It should be noted that optimal sensor sensitivity is obtained when Zsensor is approximately the same as or in the range of Zfixed.

Cell Array

FIG. 4A shows an electrical representation of cell array 24 (including cells 1–n) and the manner in which it functions to sense changes in conductivity of the aqueous mixture. As shown, each cell is coupled to Vin from signal generator 25 through an impedance element which, in this embodiment, is resistive element Ro. Referring to cell n, resistor Ro is coupled to the center sub-electrode 24D(n). The outside electrode portions 24A(n) and 24B(n) are both coupled to ground. Also shown in FIG. 4A are resistors Rs1 and Rs2 which represent the conductance of the aqueous mixture between each of the outside electrodes and the center electrode. The outside electrodes are designed to be essentially equidistant from the center electrode and consequently the conductance between each and the center electrode is essentially equal (Rs1=Rs2=Rs). As a result, Rs1 and Rs2 form a parallel resistive branch having an effective conductance of half of Rs (i.e. Rs/2). It can also be seen that resistors Ro, Rs1, and Rs2 form a voltage divider network between Vin and ground. FIG. 4B also shows the cross-section of one implementation of a cell electrode configuration with respect to a sheetmaking system in which electrodes 24A(n), 24B(n), and 24D(n) reside directly under the web 13 immersed within the aqueous mixture.

The sensor apparatus is based on the concept that the resistance Rs of the aqueous mixture and the weight/amount of an aqueous mixture are inversely proportional. Consequently, as the weight increases/decreases, Rs decreases/increases. Changes in Rs cause corresponding fluctuations in the voltage Vout as dictated by the voltage divider network including Ro, Rs1, and Rs2.

The voltage Vout from each cell is coupled to detector 26. Hence, variations in voltage directly proportional to variations in resistivity of the aqueous mixture are detected by detector 26 thereby providing information relating to the weight and amount of aqueous mixture in the general proximity above each cell. Detector 26 may include means for amplifying the output signals from each cell and in the case of an analog signal will include a means for rectifying the signal to convert the analog signal into a DC signal. In one implementation well adapted for electrically noisy environments, the rectifier is a switched rectifier including a phase lock-loop controlled by Vin. As a result, the rectifier rejects any signal components other than those having the same frequency as the input signal and thus provides an extremely well filtered DC signal. Detector 26 also typically includes other circuitry for converting the output signals from the cell into information representing particular characteristics of the aqueous mixture.

FIG. 4A also shows feedback circuit 27 including reference cell 28 and feedback signal generator 29. The concept of the feedback circuit 27 is to isolate a reference cell such that it is affected by aqueous mixture physical characteristic changes other than the physical characteristic that is desired to be sensed by the system. For instance, if water weight is desired to be sensed then the water weight is kept constant so that any voltage changes generated by the reference cell are due to physical characteristics other than water weight changes. In one embodiment, reference cell 28 is immersed in an aqueous mixture of recycled water which has the same chemical and temperature characteristics of the water in which cell array 24 is immersed in. Hence, any chemical or temperature changes affecting conductivity experienced by array 24 is also sensed by reference cell 28. Furthermore, reference cell 28 is configured such that the weight of the water is held constant. As a result voltage changes Vout(ref. cell) generated by the reference cell 28 are due to changes in the conductivity of the aqueous mixture, not the weight. Feedback signal generator 29 converts the undesirable voltage changes produced from the reference cell into a feedback signal that either increases or decreases Vin and thereby cancels out the affect of erroneous voltage changes on the sensing system. For instance, if the conductivity of the aqueous mixture in the array increases due to a temperature increase, then Vout(ref. cell) will decrease causing a corresponding increase in the feedback signal. Increasing Vfeedback increases Vin which, in turn, compensates for the initial increase in conductivity of the aqueous mixture due to the temperature change. As a result, Vout from the cells only change when the weight of the aqueous mixture changes.

One reason for configuring the cell array as shown in FIG. 3, with the center electrode placed between two grounded electrodes, is to electrically isolate the center electrode and to prevent any outside interaction between the center electrode and other elements within the system. However, it should also be understood that the cell array can be configured with only two electrodes. FIG. 5A shows a second embodiment of the cell array for use in the sensor. In this embodiment, the sensor includes a first grounded elongated electrode 30 and a second partitioned electrode 31 including sub-electrodes 32. A single cell is defined as including one of the sub-electrodes 32 and the portion of the grounded electrode 30 which is adjacent to the corresponding sub-electrode. FIG. 5A shows cells 1–n each including a sub-electrode 32 and an adjacent portion of electrode 30. FIG. 5B shows a single cell n, wherein the sub-electrode 32 is coupled to Vin from the signal generator 25 through a fixed impedance element Zfixed and an output signal Vout is detected from the sub-electrode 32. It should be apparent that the voltage detected from each cell is now dependent on the voltage divider network, the variable impedance provided from each cell and the fixed impedance element coupled to each sub-electrode 32. Hence, changes in conductance of each cell is now dependent on changes in conductance of Rs1. The remainder of the sensor functions in the same manner as with the embodiment shown in FIG. 4A. Specifically, the signal generator provides a signal to each cell and feedback circuit 27 compensates Vin for variations in conductance that are not due to the characteristic being measured.

The cells shown in FIGS. 5A and 5B may alternatively be coupled such that Vin is coupled to electrode 30 and each of sub-electrodes 32 are coupled to fixed impedance elements which, in turn, are coupled to ground.

In still another embodiment of the cell array shown in FIGS. 6A and 6B, the cell array includes first and second elongated spaced apart partitioned electrodes 33 and 34, each including first and second sets of sub-electrodes 36 and 35, (respectively). A single cell (FIG. 6B) includes pairs of adjacent sub-electrodes 35 and 36, wherein sub-electrode 35 in a given cell is independently coupled to the signal generator and sub-electrode 36 in the given cell provides Vout to a high impedance detector amplifier which provides Zfixed. This embodiment is useful when the material residing between the electrodes functions as a dielectric making the sensor impedance high. Changes in voltage Vout is then dependent on the dielectric constant of the material. This embodiment is conducive to being implemented at the dry end (FIG. 2A) of a sheetmaking system (and particularly beneath and in contact with continuous sheet 18) since dry paper has high resistance and its dielectric properties are easier to measure.

In a physical implementation of the sensor shown in FIG. 1A for performing individual measurements of more than one area of a material, one electrode of the sensor is grounded and the other electrode is segmented so as to form an array of electrodes (described in detail below). In this implementation, a distinct impedance element is coupled between Vin and each of the electrode segments. In an implementation for performing individual measurements of more than one area of a material of the sensor, the positions of the fixed impedance element and Zsensor are reversed from that shown in FIG. 1A. One electrode is coupled to Vin and the other electrode is segmented and coupled to a set of distinct fixed impedances which, in turn, are each coupled to ground. Hence, neither of the electrodes are grounded in this implementation of the sensor.

FIG. 3 illustrates a block diagram of one implementation of the sensor apparatus including cell array 24, signal generator 25, detector 26, and optional feedback circuit 27. Cell array 24 includes two elongated grounded electrodes 24A and 24B and center electrode 24C spaced apart and centered between electrodes 24A and 24B and made up of sub-electrodes 24D(1)–24D(n). A cell within array 24 is defined as including one of sub-electrodes 24D situated between a portion of each of the grounded electrodes 24A and 24B. For example, cell 2 includes sub-electrode 24D(2) and grounded electrode portions 24A(2) and 24B(2). For use in the system as shown in FIG. 2, cell array 24 resides beneath and in contact with supporting web 13 and can be positioned either parallel to the machine direction (MD) or to the cross-direction (CD) depending on the type of information that is desired. In order to use the sensor apparatus to determine the weight of fiber in a wetstock mixture by measuring its conductivity, the wetstock must be in a state such that all or most of the water is held by the fiber. In this state, the water weight of the wetstock relates directly to the fiber weight and the conductivity of the water weight can be measured and used to determine the weight of the fiber in the wetstock.

Each cell is independently coupled to an input voltage (Vin) from signal generator 25 through an impedance element Zfixed and each provides an output voltage to voltage detector 26 on bus Vout. Signal generator 25 provides Vin. In one embodiment Vin is an analog waveform signal, however other signal types may be used such as a DC signal. In the embodiment in which signal generator 25 provides a waveform signal it may be implemented in a variety of ways and typically includes a crystal oscillator for generating a sine wave signal and a phase lock loop for signal stability. One advantage to using an AC signal as opposed to a DC signal is that it may be AC coupled to eliminate DC off-set.

Detector 26 includes circuitry for detecting variations in voltage from each of the sub-electrodes 24D and any conversion circuitry for converting the voltage variations into useful information relating to the physical characteristics of the aqueous mixture. Optional feedback circuit 27 includes a reference cell also having three electrodes similarly configured as a single cell within the sensor array. The reference cell functions to respond to unwanted physical characteristic changes in the aqueous mixture other than the physical characteristic of the aqueous mixture that is desired to be measured by the array. For instance, if the sensor is detecting voltage changes due to changes in water weight, the reference cell is configured so that it measures a constant water weight. Consequently, any voltage/conductivity changes exhibited by the reference cell are due to aqueous mixture physical characteristics other than weight changes (such as temperature and chemical composition). The feedback circuit uses the voltage changes generated by the reference cell to generate a feedback signal (Vfeedback) to compensate and adjust Vin for these unwanted aqueous mixture property changes (to be described in further detail below). The non-weight related aqueous mixture conductivity information provided by the reference cell may also provide useful data in the sheetmaking process.

Cell array 24 can be readily employed in the system of FIGS. 2A and 2B so that each of the individual cells (1 to n) corresponds to each of the $UW^3$ sensors (or elements) 20A–20F. The length of each sub-electrode (24D (n)) determines the resolution of each cell. Typically, its length ranges from 1 in. to 6 in.

The array 20 is positioned underneath the web, preferably upstream of the dry line, which on a fourdrinier, typically is a visible line of demarcation corresponding to the point where a glossy layer of water is no longer present on the top of the stock.

A method of constructing the array is to use a hydrofoil or foil from a hydrofoil assembly as a support for the components of the array. In a preferred embodiment, the grounded electrodes and center electrodes each has a surface that is flushed with the surface of the foil.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A system for determining a physical characteristic including at least one of water weight, temperature, and chemical composition along the cross direction of a sheet of fibrous material that is formed on a de-watering machine that includes a water permeable moving fabric supporting wet stock comprising an aqueous fibrous mixture and a dry end which system comprises:

an array of water weight sensors (array) that is positioned underneath and adjacent to the fabric wherein the array of water weight sensors is positioned to extend transversely to and below the moving fabric supporting the wet stock wherein each water weight sensor detects resistive impedance changes to provide a detected value that is proportional to changes in the physical characteristic and the array generates signals indicative of a profile made up of a multiplicity of detected value measurements at different locations in the cross direction wherein the profile of the detected value measurements is decoupled from machine direction variations.

2. The system as defined in claim 1 further comprising a scanning sensor that is positioned at the dry end to measure the basis weight of the sheet of material at the dry end and that generates signals indicative of a profile of a cross directional multiplicity of dry basis weight measurements.

3. The system as defined in claim 2 wherein the detected value is proportional to water weight and the system further comprising means for developing a functional relationship between water weight of the sheet of material as measured by the array and the dry basis weight of the sheet material as measured by the scanning sensor and further comprising means for adjusting the functional relationship using readings from the scanning sensor to compensate for variations caused by changes in operating conditions.

4. The system as defined in claim 3 further comprising means for correlating positional readings of the scanning sensor with measurements from the corresponding sensor in the array to obtain separate calibration for each individual sensor of the array.

5. The system as defined in claim 1 wherein each water weight sensor includes a first electrode and a second electrode which is spaced-apart and adjacent to said first electrode, a portion of said wet stock being between and in close proximity to said first and said second electrodes, each sensor being coupled in series with an impedance element between an input signal and a reference potential and wherein fluctuations in the physical characteristic of said wet stock cause changes in the resistive impedance detected by each sensor.

6. The system as defined in claim 5 wherein said first electrode is coupled to said impedance element and said second electrode is coupled to said reference potential.

7. The system as defined in claim 6 wherein said first electrode is coupled to said input signal and said second electrode is coupled to said impedance element.

8. The system as defined in claim 7 wherein said second electrode comprises a set of electrically isolated sub-electrodes and said impedance element comprises a plurality of resistive elements, wherein said first electrode is coupled to said input signal and each of said set of sub-electrodes is coupled to one of said plurality of resistive elements.

9. The system as defined in claim 6 wherein said impedance element comprises a plurality of resistive elements and said first electrode comprises a plurality of electrically isolated sub-electrodes which are each coupled to one of said plurality of resistive elements.

10. The system as defined in claim 6 wherein each sensor further includes a third electrode coupled to said reference potential, said first electrode being spaced-apart and residing between said second and said third electrodes, wherein another portion of said wet stock is between and in close proximity to said first and said third electrodes.

11. The system as defined in claim 5 further comprising means for providing a feedback signal to adjust said input signal such that said fluctuations in the physical characteristic are due to fluctuations in the resistive impedance of said wet stock.

12. The system as defined in claim 5 wherein said impedance element is one of an inductive element and capacitive element each having an associated impedance and said input signal has an associated frequency and wherein said associated impedance of said one of said inductive and capacitive element is set to a particular magnitude by adjusting said associated frequency to a given magnitude.

13. The system as defined in claim 12 wherein each sensor has an associated impedance and said associated frequency is adjusted such that said sensor impedance and said impedance of said one of said capacitive element and said inductive element are approximately equal.

14. A system of controlling the cross directional basis weight uniformity of a sheet of fibrous material that is formed on a de-watering machine that includes a water permeable moving fabric supporting wet stock comprising an aqueous fibrous mixture, a dry end, and a headbox having a plurality of slices through which wet stock is introduced onto the fabric, which system comprises:

a) an array of water weight sensors that is positioned underneath and adjacent to the fabric wherein the array is positioned in a transverse direction to the moving fabric supporting the wet stock wherein each water weight sensor detects resistive impedance changes to provide a detected value that is proportional to changes in a physical characteristic of the wetstock and the array generates signals indicative of a profile made up of a multiplicity of detected value measurements at different locations in the cross direction;

b) a scanning sensor that is positioned at the dry end to measure the basis weight of the sheet of fibrous material as it enters the dry end and that generates signals indicative of a profile of a multiplicity of dry basis weight measurements in the cross direction;

c) means for developing a functional relationship between said detected value measurements and said dry basis weight measurements; and d) means for controlling the cross directional basis weight uniformity of the sheet of fibrous material by adjusting the wet stock water weight of the sheet of fibrous material along the cross direction.

15. The system as defined in claim 14 further comprising a process control system for analyzing said water weight measurement profile and said dry basis weight measurement profile and generating system control information wherein said process control system includes means for generating a control profile in response to said water weight measurement profile and said dry weight measurement profile along with physical configuration information of said system, said control profile providing control information relating to cross-directional variations of said system.

16. The system as defined in claim 14 further comprising means for adjusting the functional relationship in response to subsequent water weight and dry basis weight measurements.

17. The system as defined in claim 14 wherein the means for controlling the cross directional basis weight uniformity comprises means for adjusting the amount of wet stock discharged from the plurality of slices.

18. A method of monitoring the basis weight of a sheet of fibrous material that is formed in a process that employs a de-watering machine that includes a water permeable moving fabric supporting wet stock comprising an aqueous fibrous mixture and a dry end which comprises the steps of:

a) positioning an array of water weight sensors (array) underneath and adjacent to the fabric wherein the array is positioned in a cross direction to the moving fabric and wherein each water weight sensor detects resistive impedance changes that are proportional to changes in water weight of the wetstock;

b) positioning a scanning sensor at the dry end to measure the dry basis weight of the sheet of fibrous material;

c) operating the machine and measuring the water weights of the wetstock fibrous with the array to generate a first cross directional profile of the water weight that is decoupled from machine direction variations and measuring the dry basis weight of the sheet of fibrous material to generate a second cross directional profile of dry basis weight measurements; and d) developing a functional relationship between the first and second cross directional profiles; and e) applying readings from the first profile to control at least one process parameter to regulate the water weight of the wet stock in the cross direction on the fabric.

19. The method as defined in claim 18 further comprising the step of:

f) periodically, adjusting the functional relationship using readings from the scanning sensor to compensate for variations due to changes in operating parameters of the de-watering machine.

20. The method as defined in claim 19 wherein the de-watering machine comprises a headbox having actuators that control the discharge of wet stock through a plurality of slices and wherein the feedback mechanism controls the discharge of wet stock through the slices.

21. The method as defined in claim 19 further comprising the step of correlating positional readings of the scanning sensor with measurements from a corresponding sensor in the array to obtain separate calibration for each individual sensor of the array and step f comprises adjusting the functional relationship obtained in step d and the calibration obtained to compensate for variations due to chants in operating parameters.

22. The method as defined in claim 19 wherein each sensor including a first electrode and a second electrode which is spaced-apart and adjacent to said first electrode, said wetstock being between and in close proximity to said first and said second electrodes, each sensor being coupled in series with said impedance element between an input signal and a reference potential and wherein fluctuations in the water weight of said wetstock causes changes in the resistive impedance detected by said sensor.

23. The method as defined in claim 22 wherein said first electrode is coupled to said impedance element and said second electrode is coupled to said reference potential.

* * * * *